United States Patent
Yao et al.

(10) Patent No.: US 6,992,227 B1
(45) Date of Patent: *Jan. 31, 2006

(54) PROCESS FOR PRODUCING 1,1-BIS(4-HYDROXYPHENYL)-3,3,5-TRIMETHYLCYCLOHEXANE

(75) Inventors: Kazuhiko Yao, Wakayama (JP); Kenji Ekawa, Wakayama (JP); Yoichiro Isota, Wakayama (JP); Toru Nakaguchi, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/363,797

(22) PCT Filed: Sep. 11, 2000

(86) PCT No.: PCT/JP00/06204

§ 371 (c)(1),
(2), (4) Date: Mar. 7, 2003

(87) PCT Pub. No.: WO02/22533

PCT Pub. Date: Mar. 21, 2002

(51) Int. Cl.
*C07L 39/17* (2006.01)
(52) U.S. Cl. .................................................. 568/721
(58) Field of Classification Search ................ 568/721
See application file for complete search history.

(56) References Cited

U.S. PATENT DOCUMENTS 6,673,974 B1 * 1/2004 Yao et al. .................... 568/721

FOREIGN PATENT DOCUMENTS

| EP | 0 481 287 | 4/1992 |
| EP | 0 995 737 | 4/2000 |
| JP | 9-278697 | 10/1997 |
| JP | 2000-159710 | 6/2000 |

* cited by examiner

*Primary Examiner*—Cecilia J. Tsang
*Assistant Examiner*—Taylor Victor Oh
(74) *Attorney, Agent, or Firm*—Hamre, Schumann, Mueller & Larson, P.C.

(57) ABSTRACT

A process for production of 1,1-bis(4-hydroxyphenyl)-3,3,5-trimethylcyclohexane which comprises reacting phenol with 3,3,5-trimethylcyclohexanone in the presence of an acid catalyst, separating the resulting phenol adduct crystals of 1,1-bis(4-hydroxyphenyl)-3,3,5-trimethylcyclohexane from the resulting reaction mixture, and removing the phenol from the phenol adduct crystals, wherein the phenol adduct crystals are dissolved in a crystallization solvent comprising an aromatic hydrocarbon solvent and water, crystallizing the crystals of 1,1-bis(4-hydroxyphenyl)-3,3,5-trimethylcyclohexane out of the crystallization solvent, and collecting the crystals by filtration at a temperature of 40–60° C.

6 Claims, No Drawings

PROCESS FOR PRODUCING 1,1-BIS(4-HYDROXYPHENYL)-3,3,5-TRIMETHYLCYCLOHEXANE

TECHNICAL FIELD

The invention relates to a process for production of 1,1-bis(4-hydroxyphenyl)-3,3,5-trimethylcyclohexane (referred to as "BPTMC" hereinafter). More particularly, the invention relates to a process for production of BPTMC by an acid condensation reaction of phenol with 3,3,5-trimethylcyclohexanone (referred to as "TMC" hereinafter) wherein phenol adducts crystals of BPTMC obtained as the reaction product are crystallized out of a crystallization solvent and collected by filtration thereby providing high purity BPTMC which is remarkably reduced in the amount of not only residual phenol but also trace impurities of sodium, chlorine and sulfur in a stable manner.

BACKGROUND ART

In recent years, BPTMC is used as raw materials for the production of optical products such as optical disks, as well as synthetic resins for optical use such as polycarbonate resins for optical use. In order to supply BPTMC to this use, it is demanded to produce uncolored high purity BPTMC which is free of by-products, and besides free of high boiling point by-products or colored by-products derived from purification processes for the obtained reaction product and residual phenol or trace impurities such as sodium in high selectivity and in high yield in an industrially stable manner.

A variety of processes for the production of BPTMC are already known. According to one of such processes, phenol is reacted with TMC in the presence of an acid catalyst, and after the completion of the reaction, the resulting reaction mixture is neutralized, followed by removing water therefrom and cooling to crystallize phenol adduct crystals of BPTMC and collecting the crystals by filtration. The adduct crystals are then treated to remove phenol therefrom to provide BPTMC. In order to remove phenol from the phenol adduct crystals of BPTMC, distillation or evaporation processes are usually employed. However, these processes have a fear that the resultant BPTMC is thermally deteriorated and undesirably colored.

For instance, phenol is reacted with TMC using hydrogen chloride gas as an acid catalyst and an alkyl mercaptan as a promoter in the presence of an inactive organic solvent or in the absence of a solvent and then phenol remained unreacted is removed from the reaction mixture by steam distillation, as described in Japanese Patent Application Laid-open No. 2-88634. It is also described therein that, after the reaction, water is added to the reaction mixture, and then an alkali to neutralize the reaction mixture, followed by heating, cooling and removing an aqueous phase, thereby obtaining the desired BPTMC as residue.

A further process is known, as is described in Japanese Patent Application Laid-open No. 8-505644. According to the process, phenol is reacted with TMC using hydrogen chloride gas as a catalyst and an alkyl mercaptan such as octanethiol as a promoter. After the reaction, water is added to the reaction mixture to form a slurry, and the slurry is filtered to provide 1:1 adduct crystals of BPTMC and phenol, and then adduct crystals are broken up in warm water or in an aromatic hydrocarbon solvent such as toluene to remove phenol therefrom, thereby providing the desired BPTMC.

However, nothing has been known how to obtain high purity BPTMC in a stable manner by removing phenol advantageously from phenol adduct crystals of BPTMC.

On the other hand, in respect of 2,2-bis(4-hydroxy-phenyl)propane (referred to as "bisphenol A" hereunder), some processes for purification, in particular, those for production of high purity bisphenol A by removing phenol from phenol adduct crystals of bisphenol A are already known. For example, Japanese Patent Application Laid-open No. 4-29947 describes a process as follows. Phenol adduct crystals of bisphenol A are dissolved in a mixed solvent of phenol and an aromatic hydrocarbon and then crystallized out of the solvent to provide high purity product of bisphenol A.

A further process for production for high purity bisphenol A is also known, as is described in Japanese Patent Application Laid-open No. 5-294871. According to the process, phenol adduct crystals of bisphenol A are dissolved in water and then cooled to crystallize bisphenol A out of the water, followed by recryatallization out of an aromatic hydrocarbon solvent.

However, it is difficult to predict the behavior of production of BPTMC by a condensation reaction of TMC which is an alicyclic ketone having three methyl groups in the molecule with phenol based on the behavior of production of bisphenol A by a condensation reaction of acetone and phenol. As a matter of fact, nothing has been known how to obtain highly purified product of BPTMC which is remarkably reduced in the amount of not only residual phenol but also trace impurities of sodium, chlorine and sulfur from phenol crystals of BPTMC in high yields and in a stable manner.

The invention has been accomplished to solve such problems as involved in the known processes for the production of BPTMC by an acid condensation reaction of phenol and TMC.

Therefore, it is an object of the invention to provide a process for production of BPTMC advantageously in an industrial manner in which phenol adduct crystals of BPTMC obtained as the reaction product are crystallized from a crystallization solvent to provide highly purified product of BPTMC which is remarkably reduced in the amount of residual phenol and trace impurities of sodium, chlorine and sulfur.

SUMMARY OF THE INVENTION

The invention provides a process for production of 1,1-bis(4-hydroxyphenyl)-3,3,5-trimethylcyclohexane which comprises reacting phenol with 3,3,5-trimethylcyclo-hexanone in the presence of an acid catalyst, separating the resulting phenol adduct crystals of 1,1-bis(4-hydroxy-phenyl)-3,3,5-trimethylcyclohexane from the resulting reaction mixture, and removing the phenol from the phenol adduct crystals, wherein the phenol adduct crystals are dissolved in a crystallization solvent comprising an aromatic hydrocarbon solvent and water, crystallizing the crystals of 1,1-bis(4-hydroxyphenyl)-3,3,5-trimethylcyclo-hexane out of the crystallization solvent, and collecting the crystals by filtrating at a temperature of 40–60° C.

BEST MODE FOR CARRYING OUT THE INVENTION

According to the invention, phenol is reacted with TMC in the presence of an acid catalyst (reaction step), and after the completion of the reaction, an aqueous solution of an alkali is added to the resulting reaction mixture to neutralize it while it is heated so that the resulting phenol adduct crystals of BPTMC are dissolved in the reaction mixture to form a solution. The solution is then cooled to crystallize the adduct crystals out of the solution and the crystals are collected by filtration (primary crystallization and filtration step).

The adduct crystals are added to a crystallization solvent composed of an aromatic hydrocarbon solvent and water and the mixture is heated to a temperature of 100–130° C., preferably under an increased pressure of 0.2–0.4 MPa to dissolve the adduct crystals in the crystallization solvent.

The crystallization solvent usable is not specifically limited so long as it dissolves BPTMC when the solvent is heated whilst the solvent has a reduced solubility of BPTMC when the solvent is cooled. However, an aromatic hydrocarbon solvent having a relatively low boiling point is preferred, such as benzene, toluene, xylene or ethylbenzene, among which toluene is most preferred.

The crystallization solvent is usually composed of 55–75% by weight, preferably 60–70% by weight of aromatic hydrocarbon solvent. The crystallization solvent is used usually in an amount of 150–400 parts by weight, preferably 200–300 parts by weight, in relation to 100 parts by weight of adduct crystals. When the crystallization solvent is used in an amount of more than 400 parts by weight in relation to 100 parts by weight of adduct crystals, the volume efficiency in the purification operation is low while when the crystallization solvent is used in an amount of less than 150 parts by weight in relation to 100 parts by weight of the adduct crystals, it is difficult to remove sufficiently residual phenol and trace impurities from the resulting BPTMC.

In this way, the residual phenol is easily removed from BPTMC by using the aromatic hydrocarbon solvent as a crystallization solvent, and in addition, the solubility of BPTMC in the crystallization solvent increases to improve the volume efficiency in the purification procedure by using water in combination with the aromatic hydrocarbon solvent.

According to the invention, as described above, after the adduct crystals are dissolved in the crystallization solvent, the water layer is separated from the resulting mixture by liquid—liquid separation or the like, and the obtained oily layer is cooled to crystallize BPTMC, followed by collecting the crystals by filtration, thereby providing high purity BPTMC.

By employing such a purification procedure as mentioned above, single operation usually provides desired high purity BPTMC, however, if necessary, the operation is repeated twice or more. When the operation is repeated, the yield of the product decreases accordingly.

The crystals of BPTMC are crystallized out of the oily substance at a temperature of 70–100° C., preferably at a temperature of 80–90° C. When the temperature is too low, the purification efficiency is low, while when the temperature is too high, the purity of the product obtained is low.

According to the invention, the temperature at which the crystallized BPTMC crystals are collected by filtration in order to keep the amount of the residual phenol in the BPTMC crystals at a low level stably. The filtration temperature is preferably in the range of 40–60° C., more preferably in the range of 45–55° C. When the filtration temperature is too low, the resulting BPTMC crystals contain undesirably not a small amount of residual phenol, and the amount increases as the filtration takes a long time. When the filtration temperature is too high, the yield of desired BPTMC crystals is low.

The amount of the residual phenol in the crystals of BPTMC obtained is influenced also by the time of filtration, however, it is usually difficult to keep the time of filtration constant. According to the invention, the filtration of crystals of BPTMC are crystallized at the temperature as mentioned above so that the amount of the residual phenol in the crystals of BPTMC obtained is kept small stably if the time of filtration is varied.

INDUSTRIAL APPLICABILITY

As described above, according to the invention, phenol is reacted with 3,3,5-trimethylcyclohexanone in the presence of an acid catalyst, and the resulting phenol adduct crystals of BPTMC are crystallized out of a crystallization solvent comprised of an aromatic hydrocarbon solvent and water, in particular, at a temperature of 40–60° C. Thus, high purity BPTMC is obtained stably in which the amount of residual phenol is remarkably small, and in addition, the amount of residual phenol is not varied but substantially kept constant if the time of filtration is varied. Furthermore, the crystals of BPTMC obtained are remarkably reduced in the amount of trace impurities of sodium, chlorine and sulfur.

EXAMPLES

The invention is described in more detail with reference to examples, but the invention is not limited these examples.

Reference Example 1

188 g (2.0 mol) of phenol, 9.9 g of water and 0.5 g of 75% aqueous solution of phosphoric acid were placed in a one liter capacity four-necked flask provided with a thermometer, a dropping funnel, a reflux condenser and a stirrer. The resulting mixture was adjusted at a temperature of 20° C. After the inside the flask was replaced by nitrogen gas, hydrogen chloride gas was introduced into the flask under stirring. The gas composition in the flask was analyzed and the volume concentration of hydrogen chloride gas was adjusted at 80%.

21 g of 15% aqueous solution of sodium methyl mercaptide was added dropwise to the mixture while the mixture was maintained at a temperature of 20° C., and then a mixture of 188 g (2.0 mol) of phenol and 70.0 g (0.5 mol) of TMC was added dropwise to the mixture over a period of three hours. After the addition, the reaction was further continued at a temperature of 20° C. for anther three hours.

After the reaction, the resulting reaction mixture was analyzed by liquid chromatography. The production yield (mol of BPTMC produced/mol of starting TMC used) was found to be 89.3%.

After the reaction, 18% aqueous solution of sodium hydroxide was added to the reaction mixture so that it was neutralized to have a pH of 6.5 while it was maintained at a temperature of 40–50° C. The thus neutralized reaction mixture was heated to a temperature of 95° C. so that the formed phenol adduct crystals of BPTMC were dissolved therein.

Water was removed from the reaction mixture, and the resulting oily substance was cooled to a temperature of 30° C. to crystallize phenol adduct crystals of BPTMC. 177.9 g of the adduct crystals were collected by filtration.

The adduct crystals were found to be composed of 133.4 g of BPTMC, 44.2 g of phenol and 0.3 g of others by liquid chromatographic analysis. The adduct crystals were further found to contain trace impurities of 170 ppm of sodium (atomic absorption spectrometry), 200 pm of chlorine (inductively coupled plasma spectrometry) and 30 ppm of sulfur (inductively coupled plasma spectrometry).

Example 1

177.9 g of phenol adduct crystals of BPTMC obtained in Reference Example 1, 266.9 g of toluene and 88 g of water were placed in one liter capacity autoclave provided with a thermometer, a manometer and stirrer. After the inside atmosphere of the autoclave was replaced by nitrogen gas, the autoclave was closed, and then the inside was raised to a temperature of 120° C. with stirring to dissolve the adduct crystals in the mixture. The stirring was then stopped, and the mixture was left standing for 30 minutes. The water layer was separated by liquid—liquid separation, and the obtained oily layer was cooled to a temperature of 50° C. so that BPTMC was crystallized, and immediately the oily substance was centrifuged to obtain BPTMC crystals while the oily substance was kept at a temperature of 50° C.

The thus obtained BPTMC crystals were dried at a temperature of 110° C. under a pressure of 20 mmHg for four hours to evaporate the solvent to provide 111.5 g of high purity BPTMC crystals. The yield was 83.55% based on the adduct crystals.

The BPTMC crystals were found to have a purity of 99.9% and a phenol content of 100 ppm by liquid chromatographic analysis. The crystals were further found to contain trace impurities of 0.4 ppm of sodium (atomic absorption spectrometry), 0.27 ppm of chlorine (inductively coupled plasma spectrometry) and 0.6 ppm of sulfur (inductively coupled plasma spectrometry).

The analytical results of the high purity BPTMC crystals obtained are shown in FIG. 1 together with the time during which the oily substance was held at the predetermined temperature (holding time) and the predetermined temperature at which the crystals of BPTMC were filtrated (filtration temperature).

Example 2

129.4 g of phenol adduct crystals of BPTMC, 194.2 g of toluene and 97.1 g of water were used and, after the oily substance obtained was held at a temperature of 50° C. for 16 hours, it was centrifuged at the same temperature, and otherwise in the same manner as in Example 1, high purity BPTMC crystals were obtained. The results are shown in Table 1.

Example 3

129.4 g of phenol adduct crystals of BPTMC, 194.2 g of toluene and 97.1 g of water were used and, after the oily substance obtained was held at a temperature of 50° C. for 40 hours, it was centrifuged at the same temperature, and otherwise in the same manner as in Example 1, high purity BPTMC crystals were obtained. The results are shown in Table 1.

Comparative Example 1

129.4 g of phenol adduct crystals of BPTMC, 194.2 g of toluene and 97.1 g of water were used and, after the oily substance obtained was held at a temperature of 30° C. for 22 hours, it was centrifuged at the same temperature, and otherwise in the same manner as in Example 1, high purity BPTMC crystals were obtained. The results are shown in Table 1.

Comparative Example 2

129.4 g of phenol adduct crystals of BPTMC, 194.2 g of toluene and 97.1 g of water were used and, after the oily substance obtained was held at a temperature of 30° C. for 48 hours, it was centrifuged at the same temperature, and otherwise in the same manner as in Example 1, high purity BPTMC crystals were obtained. The results are shown in Table 1.

Comparative Example 3

129.4 g of phenol adduct crystals of BPTMC, 194.2 g of toluene and 97.1 g of water were used and, immediately after the oily substance obtained was cooled to a temperature of 30° C., it was centrifuged, and otherwise in the same manner as in Example 1, high purity BPTMC crystals were obtained. The results are shown in Table 1.

Comparative Example 4

129.4 g of phenol adduct crystals of BPTMC, 194.2 g of toluene and 97.1 g of water were used and, immediately after the oily substance obtained was cooled to a temperature of 25° C., it was centrifuged, and otherwise in the same manner as in Example 1, high purity BPTMC crystals were obtained. The results are shown in Table 1.

TABLE 1

|  | Examples | | | Comparative Examples | | | |
| --- | --- | --- | --- | --- | --- | --- | --- |
|  | 1 | 2 | 3 | 1 | 2 | 3 | 4 |
| Treating Conditions of Oily Substance | | | | | | | |
| Filtration Temperature (° C.) | 50 | 50 | 50 | 30 | 30 | 30 | 25 |
| Holding Time (hr) | 0 | 16 | 40 | 22 | 48 | 0 | 40 |
| Quality of Purified BPTMC | | | | | | | |
| Purity (%) | 99.9 | 99.9 | 99.9 | 99.7 | 99.4 | 99.8 | 99.8 |
| Phenol (ppm) | 100 | 120 | 140 | 1600 | 5900 | 290 | 400 |
| Na (ppm) | 0.4 | 0.3 | 0.8 | 3.7 | 10.0 | 2.1 | 9.1 |
| Cl (ppm) | 0.27 | 0.5 | 0.7 | 10.0 | 9.9 | 5.5 | 3.9 |
| S (ppm) | 0.6 | 0.6 | 0.6 | 0.6 | 0.7 | 0.6 | 1.4 |

The invention claimed is:

1. A process for production of 1,1,-bis(4-hydroxyphenyl) 3,3,5-trimethylcyclohexane which comprises reacting phenol with 3,3,5-trimethylcyclohexanone in the presence of an acid catalyst, separating the resulting phenol adduct crystals of 1,1-bis(4-hydroxyphenyl)-3,3,5-trimethylcyclohexane from the resulting reaction mixture, and removing the phenol from the phenol adduct crystals, wherein the phenol adduct crystals are dissolved in a crystallization solvent comprising an aromatic hydrocarbon solvent and water, crystallizing the crystals of 1,1-bis(4-hydroxyphenyl)-3,3,5-trimethylcyclohexane out of the crystallization solvent, and collecting the crystals by filtration at temperature of 40–60° C.

2. The process as claimed in claim 1, wherein the crystals of 1,1-bis(4-hydroxyphenyl)-3,3,5-trimethylcyclohexane are collected by filtration at a temperature not lower than 45° C.

3. The process as claimed in claim 1, wherein the amount of the aromatic hydrocarbon solvent in the crystallization solvent is in the range of 55–75% by weight.

4. The process as claimed in claim 1, wherein the crystallization solvent is used in an amount of 150–400 parts by weight in relation to 100 parts by weight of the phenol adduct crystals.

5. The process as claimed in claim 1, wherein the aromatic hydrocarbon solvent is at least one selected from the group consisting of benzene, toluene, xylene and ethylbenzene.

6. The process as claimed in claim 1, wherein the crystallization solvent consists essentially of an aromatic hydrocarbon solvent and water.

* * * * *